US00PP14450P29

(12) United States Plant Patent
Morris

(10) Patent No.: US PP14,450 P2
(45) Date of Patent: Jan. 6, 2004

(54) MINT PLANT NAMED 'CLACKAMAS'

(50) Latin Name: *Mentha×piperita*
Varietal Denomination: Clackamas

(75) Inventor: Mark Morris, Eugene, OR (US)

(73) Assignee: A.M. Todd Company, Kalamazoo, MI (US)

( * ) Notice: Subject to any disclaimer, the term of this patent is extended or adjusted under 35 U.S.C. 154(b) by 0 days.

(21) Appl. No.: 10/193,213

(22) Filed: Jul. 12, 2002

(51) Int. Cl.[7] ..... A01H 5/00
(52) U.S. Cl. ..... Plt./259
(58) Field of Search ..... Plt./259, 258

*Primary Examiner*—Bruce R. Campell
*Assistant Examiner*—June Hwu
(74) *Attorney, Agent, or Firm*—Kramer & Amado, P.C.

(57) ABSTRACT

A new and distinct peppermint plant 'Clackamas' characterized by its resistance to Mint rust (*Puccinia menthe* Pers), Mint wilt (*Ferticillium dahliae* and *Verticillium albo-atrum*), and Spider mites as well as a more upright growth habit and a lighter green color the Black Mitcham peppermint plant.

3 Drawing Sheets

Latin name of the genus and species of the plant claimed: *Mentha×piperita.*
Variety denomination: 'Clackamas'.

FIELD OF THE INVENTION

The present invention relates to a new and distinct peppermint plant botanically known as *Mentha×piperita*. The new variety has been named 'Clackamas' and will be referred as such hereafter.

BACKGROUND OF THE INVENTION

The new peppermint plant of the present invention was developed in an effort to cultivate a peppermint variety exhibiting an upright growth habit, vigorous and abundant root growth, greater resistance to Mint rust (*Puccinia menthe* Pers), Verticillium wilt (*Verticillium dahliae* and *V. albo-atrum*), and Spider mites (*Tetranychus urticae*). Further, 'Clackamas' produces a peppermint oil that varies minimally in oil profile based on plant maturity.

The inventor explored ways of creating peppermint hybrids through conventional crosses from the 'Black Mitcham' (*Mentha piperita*)—not patented—parent plants without the use of chemicals to increase ploidy. The method relied on adjusting environmental conditions to generate viable pollen. Using this method, several seedlings were generated in 1996 using two 'Black Mitcham' peppermint plants as parents.

The resulting selection has been under continuous evaluation at the A. M. Todd facility located in Jefferson, Oreg. since 1996 and has been asexually propagated through propagules and rhizome cuttings. The resulting propagules have remained identical to the parent plant regarding resistance to the common diseases encountered by mint plants in general and exhibiting heartier and more upright growth habit as compared to 'Black Mitcham.'

SUMMARY OF THE INVENTION

The present invention relates to a novel mint plant named 'Clackamas' characterized by its more upright growth habit as shown by taller growth with thicker stems, when compared to commercial peppermint varieties, more abundant and vigorous root growth and resistance to Mint rust (*Puccinia menthe* Pers), Verticillium wilt (*Verticillium dahliae* and *V. albo-atrum*), and Spider mites (*Tetranychus urticae*), and more upright growth habit as shown by taller growth with thicker stems, larger leaves and a lighter green color, when compared to 'Black Mitcham.' The peppermint oil profile of 'Clackamas' is also similar throughout its maturity when grown in Oregon and Washington.

BRIEF DESCRIPTION OF THE PHOTOGRAPHS

Figure 1:
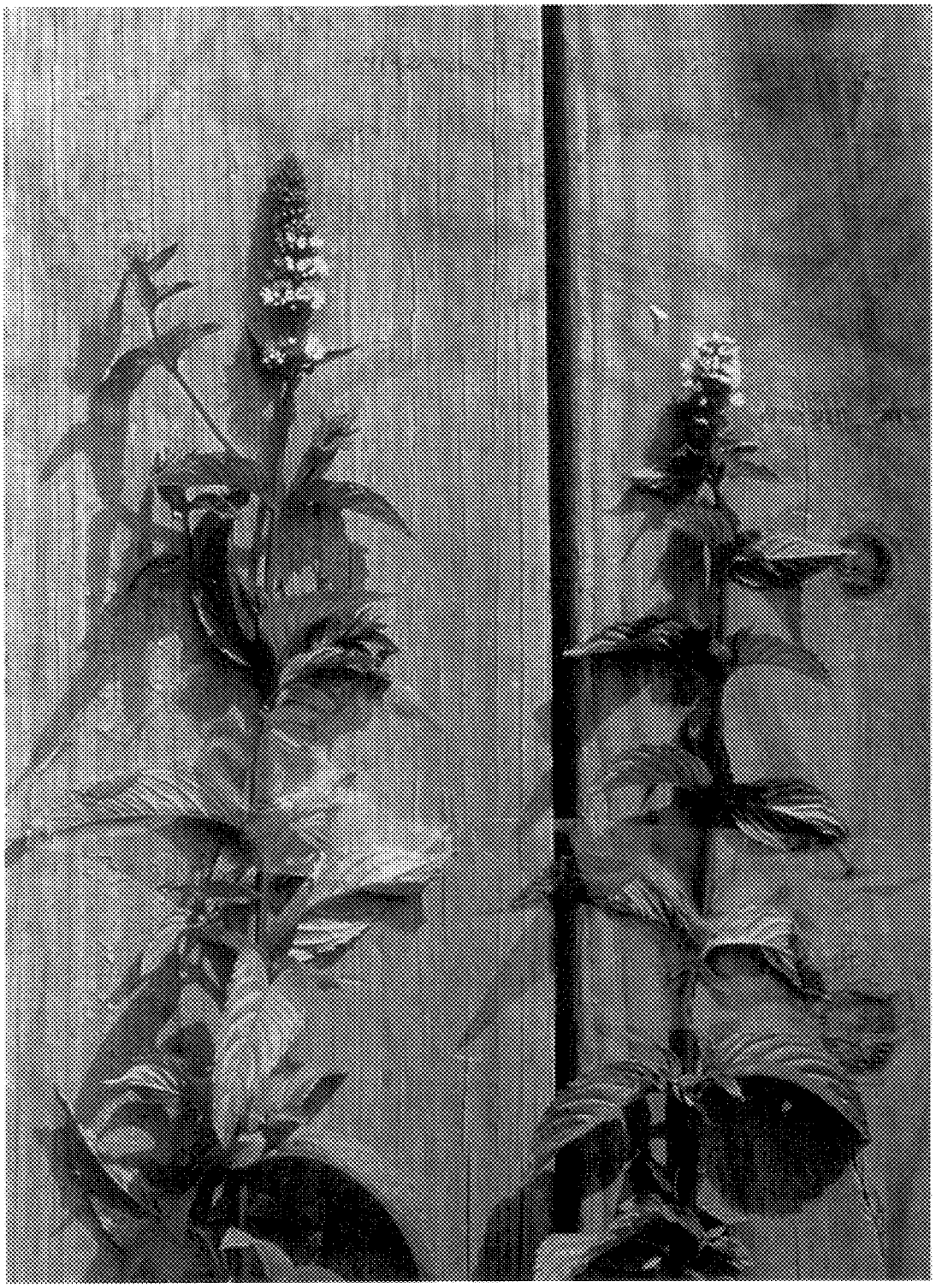

The accompanying color photographs of 'Clackamas' show the new variety:

FIG. 1: shows cuttings of the claimed plant 'Clackamas' including its foliage and inflorescences.

Figure 2:
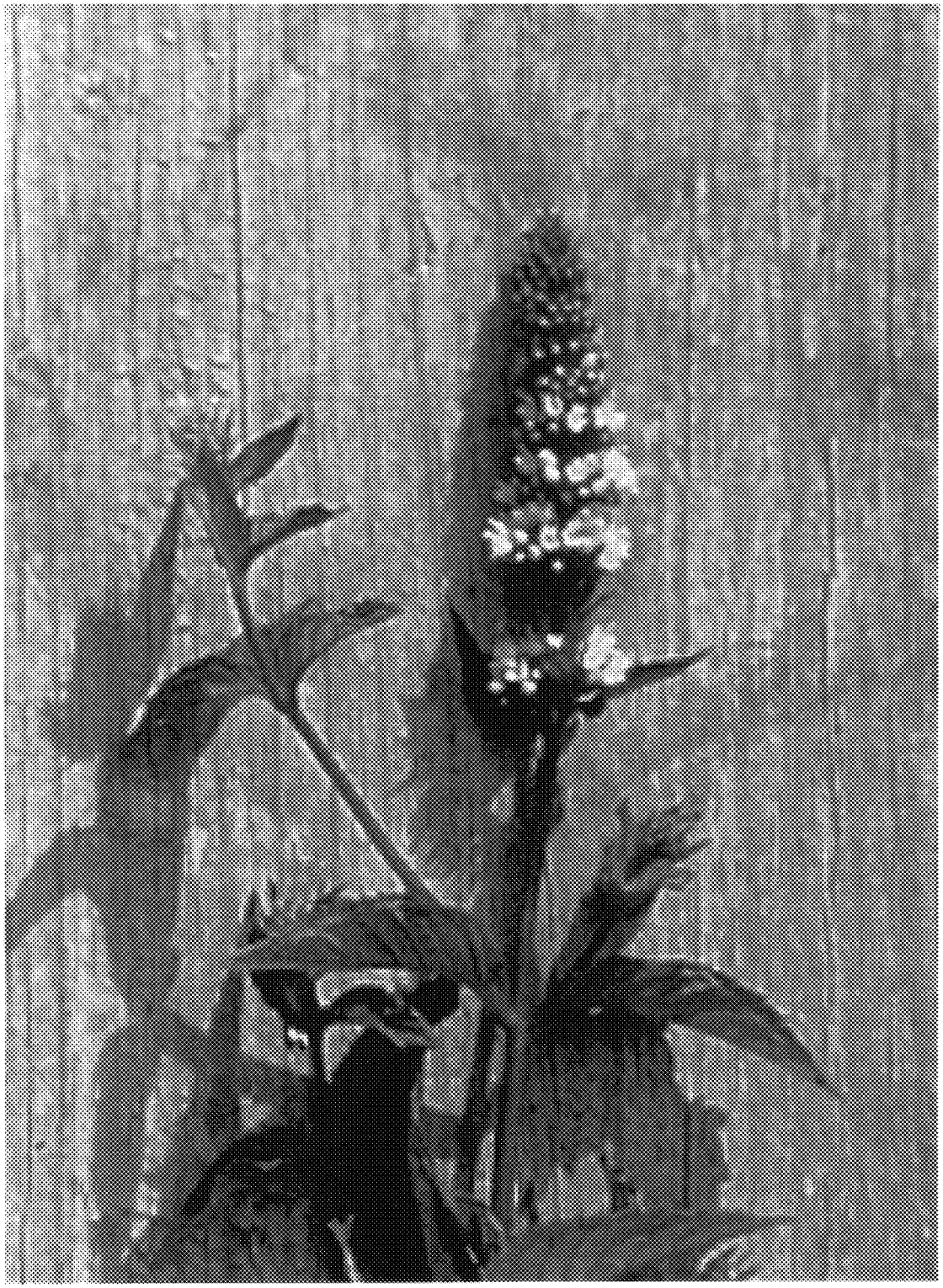

FIG. 2: shows the flower spike of 'Clackamas.'

Figure 3:
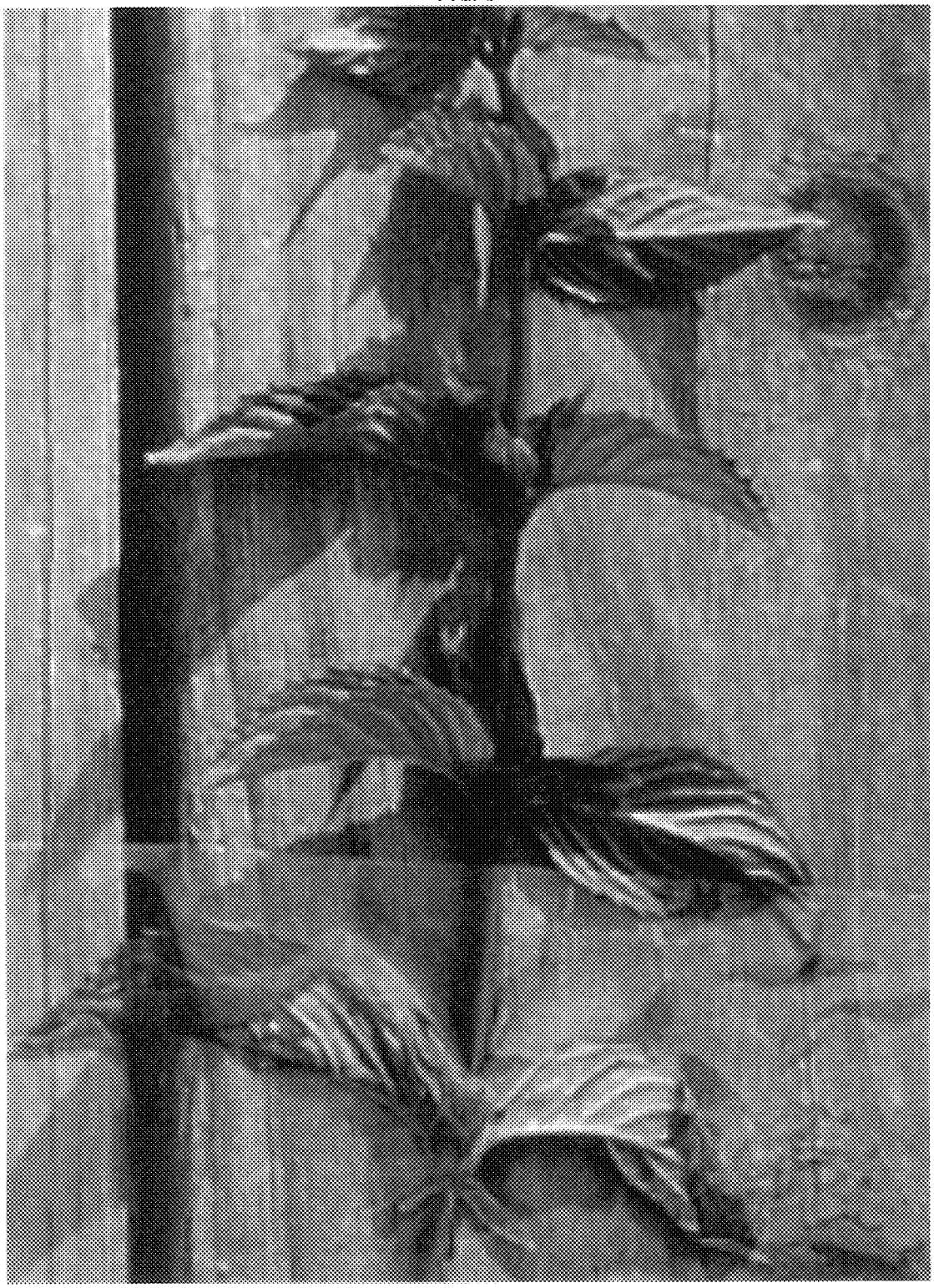

FIG. 3: shows the mature leaves of 'Clackamas.'

DETAILED DESCRIPTION OF THE INVENTION

The present invention is a new and distinct variety of a *Mentha×piperita* peppermint plant having the following characteristics that, in combination, are not exhibited in other peppermint plants:

1. More upright growth habit;
2. More vigorous and abundant root growth;
3. Oil profile that shows little variability based on plant maturity;
4. Improved resistance to Mint rust (*Puccinia menthe* Pers);
5. Improved resistance to Verticillium wilt (*Verticillium dahliae* and *V. albo-atrum*);
6. Improved resistance to Spider mites (*Tetranychus urticae*); and
7. A lighter green color.

'Clackamas' is an herbaceous perennial with an upright shrubby growth habit. The observed plants were two years old and were grown outdoors in western Oregon, in a silt-loam soil. Based on initial May planting density of 8,000 plants per acre, a new 'Clackamas' rootstock field would fill in by mid-June. The density of rhizomes from this acre of rootstock allows for a 10 to 1 expansion the following season, which is similar to 'Black Mitcham.' Numerous branching stems are produced each year with an eventual height between 60–80 cm. The approximate plant spread is in the range of 12–22 cm reflecting a size measurement half way up the plant during bloom on a managed field plot. Measurements taken at different times of the year, on different locations of the plants, under different crop management regimes will vary. As 'Clackamas' is a rhizomatous perennial, it is not possible to specify the accurate dimensions of one single plant because the differentiation of where one plant terminates and another begins is unknown. At the end of one growing season, it is estimated that one rooted cutting will have spread through a four square foot area. When compared to 'Black Mitcham,' the industry standard, which is not patented and has been commercially grown for hundreds of years, 'Clackamas' is more upright in its growth habit, taller with thicker stems (due to a large extent to the highly lignified stems which reduces lodging), larger leaves and a lighter green color with less anthocyanin pigment development under similar growing conditions.

'Clackamas' has a square stem, in the range of 5 mm on a side, compare to the average 4.5 mm stem of 'Black Mitcham.' Stems and leaves, especially along leaf veins, are sparsely pubescent and more so than 'Black Mitcham.' Based on flowering 'Clackamas' matures at approximately the same time as 'Black Mitcham.' 'Clackamas' also features the additional benefit of vigorous and abundant root growth, which results in more rapid acreage expansion and reduction in planting costs. As compared to the peppemint plant 'McKenzie,' which is disclosed in co-pending application No. 10/193,191, 'Clackamas' has a shorter flower spike, thinner stems, lighter leaf color, and on average a shorter growth habit with smaller leaves.

All color descriptions according to The R.H.S. Colour Chart. In botanical terms, 'Clackamas' has ovate leaves with a serrate margin. The leaves are oppositely arranged on the stem with an equilateral base, an acute apex, and serrate margin. Ventral leaf surface color is 147A (Yellow-Green Group), dorsal color is 147B (Yellow-Green Group), petiole color is 147C (Yellow-Green Group). Stem color is 146C (Yellow-Green Group) near the base and gradually becomes more purple until the color at the apex is 187A (Greyed-Purple Group). The fragrance is peppermint-like.

In contrast to the red pigments found in 'Black Mitcham,' the leaves of 'Clackamas' are slightly narrower and also light green in color. The flower spike of 'Clackamas' is more elongated than 'Black Mitcham' under similar growing conditions and the number of paired flower whorls, or verticillasters varies from 8–15. The first internode between verticels varies from 1 to 3 cm. The individual flowers of Clackamas contain a 4-lobed, nearly regular corolla 73D (Red-Purple Group) with a short tube, 7 mm long from the base of the calyx to the tip of the forked white stigma. The calyx has an average of five ciliate teeth fused at the base forming a short tube and is 4 mm long. The calyx, peduncle and pedicel colors are 187A (Greyed-Purple Group). Each flower has one pistil with a 6 mm long white style and four epipetalous stamens that may be exerted with 3 mm long white filaments. The white anthers are less than 1 mm. Pollen color is 10D (Yellow Group). The formation of seed is a rare event. There is no obvious flower fragrance. The flower color is also whiter in color as compared to the mostly lavender 'Black Mitcham.'

The oil produced by 'Clackamas' is of a typical peppermint type. In contrast to 'Black Mitcham' the peppermint oil profile of 'Clackamas' varies little with plant maturity. This feature allows for increased yield due to flexible harvest timing during a single season without significant changes occurring to its peppermint oil profile. 'Clackamas' has an herbage yieldage of approximately 80 lbs./acre and an essential oil quality of peppermint oil having 5 to 10 percent higher level of menthyl acetate than standard 'Black Mitcham' peppermint.

'Clackamas' has been grown and observed under 3 different field conditions as well as under greenhouse conditions. As with all plants, the traits have varied depending on location. These differences can be attributed to varying climates, soils, fertilizers and water regimes. However, 'Clackamas' remains distinct from other peppermint plants in its characteristics. The resistance to the diseases identified above is presented in Table I. The results were gathered from a study performed in western Oregon and show the comparison of 'Clackamas' to 'Black Mitcham' according to the mean number of rust pustules per leaf, mean number of Verticillium strikes per plot and mean number of spider mites per leaf during three years of analysis.

TABLE I

| Variety | Mean Number of Rust Pustules per leaf | Mean Number of Verticillium strikes per plot | Mean Number of Spider Mites per leaf |
|---|---|---|---|
| Aug. 15, 1999 | | | |
| 'CLACKAMAS' | 5.00 | 0.25 | 1.00 |
| 'Black Mitcham' | 40.30 | 9.25 | 8.25 |
| Aug. 22, 2000 | | | |
| 'CLACKAMAS' | 20.25 | 1.25 | 0.38 |
| 'Black Mitcham' | 183.25 | 17.00 | 10.00 |
| Aug. 26, 2001 | | | |
| 'CLACKAMAS' | 5.75 | 2.75 | 0.00 |
| 'Black Mitcham' | 81.25 | 30.50 | 11.25 |

As illustrated by Table I, 'Clackamas' is significantly more resistant to the diseases shown. For example, although the incidence of Mint Rust varied overall according to the three years shown due to differences in annual growing conditions, 'Clackamas' consistently showed greater resistance to *Puccinia menthe* Pers when compared to the mean number of Rust Pustules per leaf. Similarly, the number of mean strikes per plot for *Verticillium dahliae* and *Verticillium albo-atrum* was markedly reduced by 'Clackamas' when compared to 'Black Mitcham'. In the case of *Tetranychus urticae*, the man number of Spider Mites per leaf was almost eliminated in comparison to 'Black Mitcham'.

While the plant identified in the present invention has been described as it relates to a specific embodiment, it is understood that this application is intended to cover other variations, uses and adaptations that may arise under different environmental conditions.

What is claimed is:

1. A new and distinct variety of *Mentha×piperita* plant named 'Clackamas' substantially as shown and described herein.

* * * * *